(12) United States Patent
Johnson

(10) Patent No.: US 6,749,755 B2
(45) Date of Patent: Jun. 15, 2004

(54) WATER SEPARATION FROM SOLVENT

(76) Inventor: Robert S. Johnson, 25 Blue Heron, Hampstead, NH (US) 03841

(*) Notice: Subject to any disclaimer, the term of this patent is extended or adjusted under 35 U.S.C. 154(b) by 0 days.

(21) Appl. No.: 10/095,296

(22) Filed: Mar. 11, 2002

(65) Prior Publication Data

US 2002/0179529 A1 Dec. 5, 2002

Related U.S. Application Data

(63) Continuation-in-part of application No. PCT/US01/20555, filed on Jun. 27, 2001.
(60) Provisional application No. 60/215,055, filed on Jun. 29, 2000.

(51) Int. Cl.[7] ............................................... B01D 61/00
(52) U.S. Cl. ..................... 210/650; 210/767; 210/416.1; 210/321.75
(58) Field of Search ................................. 210/650, 640, 210/321.75, 767, 95, 45, 416.1, 651, 321.6; 422/101; 95/52

(56) References Cited

U.S. PATENT DOCUMENTS

| | | | |
|---|---|---|---|
| 3,953,566 A | 4/1976 | Gore | 264/288 |
| 4,187,390 A | 2/1980 | Gore | 174/102 |
| 4,902,308 A * | 2/1990 | Mallouk et al. | |
| 4,909,810 A | 3/1990 | Nakao et al. | 55/16 |
| 5,268,150 A * | 12/1993 | Burkitt | |
| 5,269,933 A * | 12/1993 | Jejle et al. | |
| 5,271,846 A * | 12/1993 | Uragami et al. | |
| 5,350,519 A * | 9/1994 | Kaschemekat et al. | |
| 5,454,951 A | 10/1995 | Hoopman | 210/650 |
| 5,792,425 A | 8/1998 | Clark et al. | 422/101 |
| 5,976,380 A | 11/1999 | Moya | 210/650 |
| 6,019,920 A | 2/2000 | Clough | 264/127 |

* cited by examiner

Primary Examiner—Ana Fortuna
(74) Attorney, Agent, or Firm—Grossman, Tucker, Perreault & Pfleger, PLLC

(57) ABSTRACT

An apparatus and method for separating residual water from a solvent. The device comprises a reservoir containing a solution comprising solvent containing residual water, the reservoir having an opening to allow the solution to drain from the reservoir. A membrane layer is provided comprising a layer of fluropolymer material, said membrane material having a IPA Bubble Point of ≧25 psi. The membrane is positioned in series with the reservoir opening. Vacuum is generated on one side of the membrane layer wherein the solvent containing water passes through the membrane therein removing water from the solvent to provide a solvent with a water level of less than or equal to 1.0 ppm.

12 Claims, 3 Drawing Sheets

WATER SEPARATION FROM SOLVENT

CROSS REFERENCE TO RELATED APPLICATIONS

This application is a continuation-in-part of International Application No. PCT/US01/20555, filed Jun. 27, 2001, designating the United States, which International Application claims the benefit of U.S. Provisional Application Serial No. 60/215,055 filed Jun. 29, 2000.

FIELD OF THE INVENTION

This invention generally relates to the field of chemical laboratory equipment for sample preparation and particularly to the use of a hydrophobic membrane to separate water from an organic solvent, and more particularly to an apparatus and method for increasing the flow rate of the solvent through the membrane without adversely affecting the performance of the membrane.

BACKGROUND OF THE INVENTION

When samples are to be analyzed for organic and/or inorganic trace compounds, the samples are typically extracted with an organic solvent. The solvent extracts the compounds from the sample, due to selective chemistry.

Before the extract can be analyzed, all residual water should preferably be removed from the extracting solvent. This is due to the adverse effect residual water can have on the analytical instruments that are used to analyze the sample.

Current practice embodies the use of a drying agent called sodium sulfate and has been the standard technique to remove the residual water from solvent extracts. Sodium sulfate is a granular material that has a high binding capacity for residual water. The sodium sulfate is first heated to drive off any water that has been adsorbed into the material. This typically requires heating overnight at 400 C. The sodium sulfate is then placed into a glass funnel containing filter paper, or a chromatography column. The funnel or column is then washed with extracting solvent to wash off any impurities. The extracting solvent is then discarded. Once the sodium sulfate is clean, the solvent extract is poured on top of the sodium sulfate. As the solvent drains slowly through, the residual water becomes bound to the surface of the sodium sulfate. The collected solvent passing through is now dry and ready for analysis.

The use of sodium sulfate, even though easy to use, requires many physical manipulations. Sodium sulfate requires the use of glassware that must be subsequently washed so as not to introduce contaminants into the samples and requires the purchase of, and the disposal of, the used sodium sulfate. The labor time and the materials costs, add significantly to the total cost of performing sample extractions.

U.S. Pat. No. 5,268,150 assigned to Corning Incorporated, discloses the use of a hydrophobic membrane in an extraction device which allows a solvent to pass therethrough, yet will not allow a significant amount of water from the sample liquid to pass therethrough. The patent discloses that hydrophobic membranes incorporating polytetrafluoroethylene (PTFE) have been found to be very effective in achieving the desired results of letting solvent pass, while retaining the sample usually consisting of a relatively large portion of water or an aqueous solution. The patent goes on to state that the typical dimensions of the membrane range from 10 to 50 millimeters in diameter with a thickness ranging from 0.1 to 5.0 microns with a pore size ranging from 0.2 to 5.0 microns, depending upon the sample being processed. In addition, this patent emphasizes that the extractor design disclosed therein includes a chamber specifically for loading sodium sulfate to assist in water removal.

Attention is also directed to the following U.S. Pat. Nos. 3,953,566; 4,187,390; 4,909,810; 5,792,425; 5,454,951; 5,976,380 and 6,019,920.

Accordingly, it is an object of the invention to improve on the above referenced designs and provide a more efficient technique for separation water from a given solvent. More specifically, it is an object of the present invention to provide a method and apparatus and improved membrane design to improve the purification flow rate of a solvent/water mixture or emulsion through said membrane, to remove water, without adversely effecting membrane performance.

SUMMARY OF THE INVENTION

A method for separating residual water from a solvent, comprising the steps of providing a reservoir containing a solution comprising solvent containing residual water, the reservoir having an opening to allow the solution to drain from the reservoir, resisting the flow of the solution from the reservoir with a membrane layer comprising a layer of fluropolymer material, said membrane material having a IPA Bubble Point of $\geq 25$ psi, said membrane positioned in the series with the reservoir opening, decreasing the pressure on the second side of said supported membrane relative to the first side of said supported membrane to thereby increase the flow rate of the solvent through the membrane and therein removing said water from said solvent to provide a solvent with a water level of less than or equal to 1.0 ppm.

BRIEF DESCRIPTION OF THE DRAWINGS

The above and other objects, feature, and advantages of the present invention will be apparent in the following detailed description thereof when read in conjunction with the appended drawings wherein the same reference numerals denote the same or similar parts throughout the several views.

DETAILED DESRIPTION OF THE DRAWINGS

Figure 1:
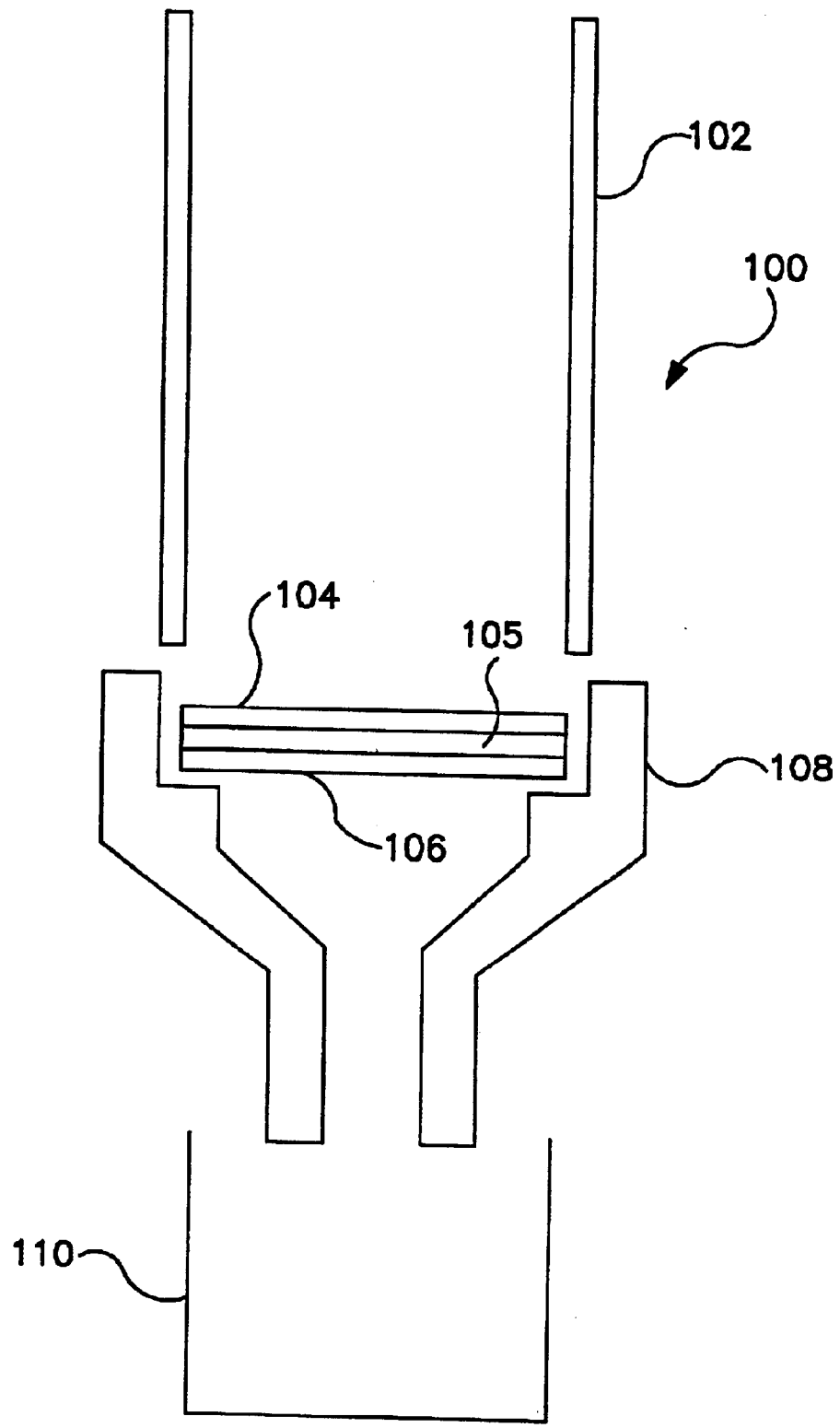
FIG. 1 is a sectional view of a first separator apparatus in accordance with the present invention.

Referring to the drawings, there is illustrated generally a first concentrator/extractor apparatus 100. The concentrator/extractor apparatus 100 comprises a column 102 and fluropolymer material layers 104 and 105. Preferably, fluropolymer layer 104 is laminated to fluropolymer layer 105 to provide a membrane type construction. A preferred fluropolymer for layer 104 is PTFE and a preferred fluropolymer for layer 105 is ethylene-chlorotrifluroethylene (ECTFE).

A screen support layer is shown at 106, in addition to a base assembly 108, and a collection vessel 110. The column 102 forms a reservoir to hold a solvent. The column 102, which may be pressed down on top of the membrane (fluropolymer layer 104 laminated to fluropolymer layer 105) may be used to hold the membrane in place. The column 102 may seal the membrane and prevent any solvent from passing around the edge of the membrane. The column 102 and the collection vessel 110 are preferably made of glass. The screen support member 106 is preferably an ECTFE or ETFE fluoropolymer fabric screen with 0.5–1.0 mm openings, 0.5–1.0 mm thick, and a 0.25–0.50 mm thread.

The membrane comprises layers 104 and 105 are preferably characterized as follows:

Pore Size: 0.05 to 0.2 micron;
Bubble Point: Individual between 15.0 psi and 23.0 psi (47 mm membrane; isopropanol at 21° C.)
WEP: 50.0 psi minimum individual
Gurley Number: Mean≦30.0 seconds (100 cc air through 1 in$^2$ orifice, 4.88" water pressure drop)
Thickness: Preferably 1.0 mils to 20 mils.

The following definitions apply to the above:

Gurley number: A measure of the air permeability of the fluropolymer. The Gurley number is the time in second required for 100 cc of air to pass through a one square inch area of membrane, when a constant pressure of 4.88 inches of water is applied.

Bubble point: The minimum pressure in KG/CM$^2$ required to force air through the fluropolymer that has been prewetted with water, isopropanol, or methanol.

Water entry pressure: The pressure at which water permeates through the membrane. This is a visual test.

In a preferred embodiment, the PTFE layer 104 has a usable diameter of 40–100 mm. The fluoropolymer layer 104 and fabric support member 105 are positioned in series between the column 102 and the collection vessel 110. In a most preferred embodiment, a 3 mil thick PTFE layer 104 with a 0.1 micron pore size is supported on a 10 mil thick non-woven layer 105, comprised of ECTFE polymer, which ECTFE polymer is preferably obtained from Ausimont and sold under the tradename "HALAR".

It is worth noting that in preferred embodiment, a 3.0 mil PTFE layer is laminated to a 10 mil ECTFE layer, and a resulting thickness of 3–7 mils is produced for the laminate as a result of the heat setting laminating process.

In accordance with the present invention, the screen layer 106 is preferably ethylene-trifluroethylene copolymer (ETFE). The screen layer serves to gap or space laminated layers 104 and 105 on the funnel surface such that it is possible to distribute the pressure differential across the entire cross-sectional area of the funnel surface to achieve more efficient performance. However, while it can be appreciated that screen layer 106 is a separate components, it can be appreciated that screen layer 106 may actually be incorporated directly into the surface of the funnel upon which the laminated layers 104 and 106 rest. This would provide the equivalent effect of spacing laminated layers 104 and 106 to evenly distribute the pressure differential created by vacuum.

Furthermore, in the context of the present invention it should be appreciated that the removal of water from a given solvent containing, e.g., some analyte to be evaluated by techniques such as gas-chromatography/mass spectrometry (GCMS), is such that the removal of water is highly efficient and allows for the generation of GCMS analysis that is not compromised by the presence of water. In that regard, it has been found that the present invention allows for removal of water down to 1.0 ppm.

Expanding upon the above, it will be appreciated that with respect to the removal of water herein, it has been found that by reference to the generation of a GCMS that is not compromised by the presence of water, it should also be understood that this is reference to the fact that the water removal herein is sufficient to reduce the water levels to that level wherein the possibility of contamination of the GC column by a water soluble inorganic acid is removed or attenuated. In addition, the possibility of any contamination of the GC column due to the presence of water soluble inorganic salts is also equally attenuated or removed, and GCMS can proceed without such problems.

Additionally, it is worth noting that the invention herein is preferably applied to a water/solvent mixture wherein the solvent is denser than water. However, in broad context the invention herein is not so limited.

Figure 2:
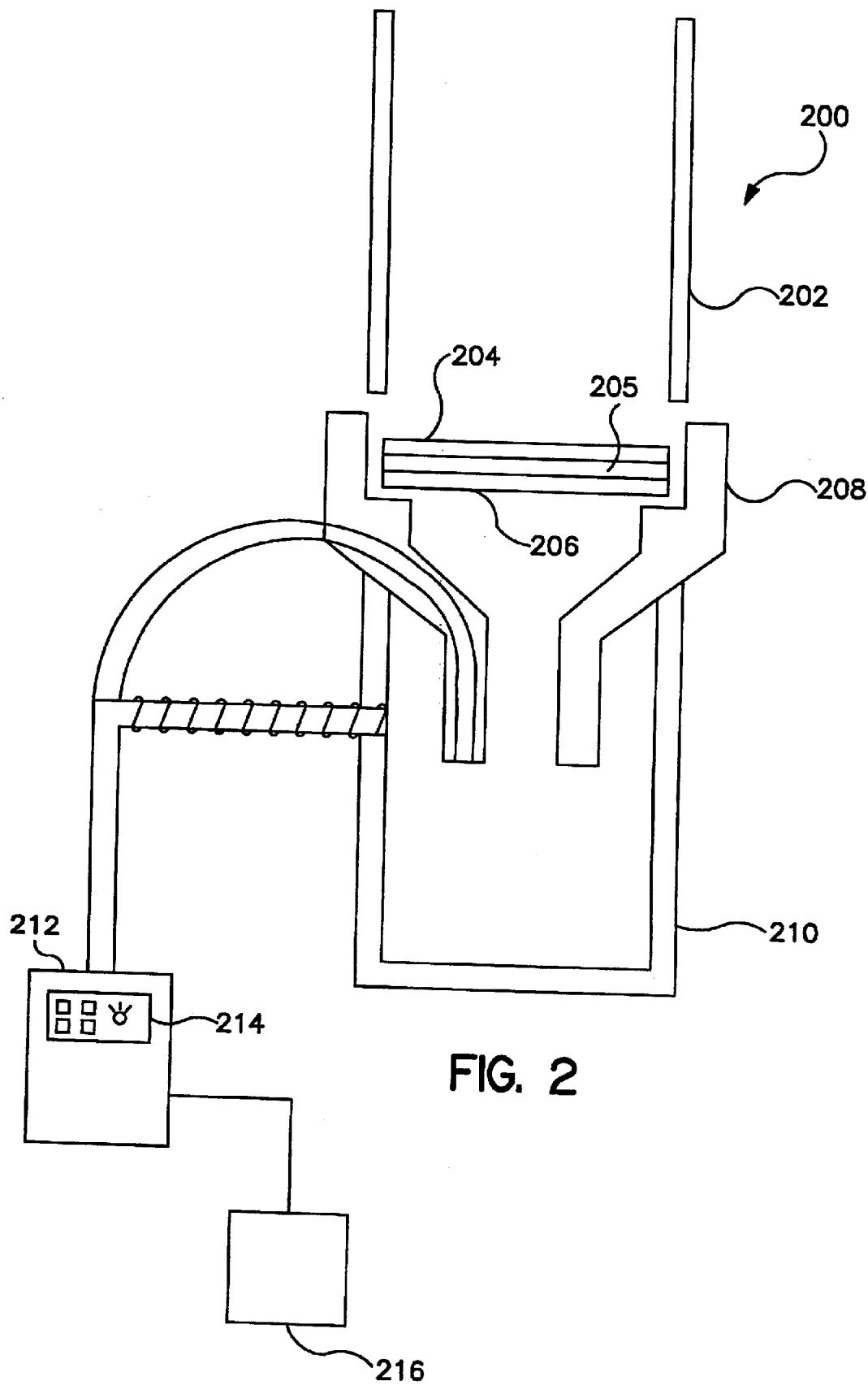
FIG. 2 is a sectional view of a second separator apparatus in accordance with the present invention.

As shown in FIG. 2, there is illustrated generally a second concentrator/extractor apparatus 200. The concentrator/extractor apparatus 200 comprises a column 202, a fluropolymer layer 204 (PTFE) and a fluropolymer layer 205 (ECTFE) that, as noted above, are preferably laminated to one another. In addtion, a support screen member 206 is shown, a base assembly 208, and a collection vessel 210. The apparatus 200 can be coupled to an external low-level vacuum 212. A low level vacuum is one that preferably creates a pressure drop of less than 6" Hg. Alternatively, the assembly 200 could include a vacuum generator device that uses a compressed gas source to create a pressure differential. This assembly could be manufactured as a unit and could sit in a hood, directly underneath a separatory funnel. Once the gas source is set, the operator may select one of a plurality of vacuum levels on a vacuum level selector panel 214. The vacuum selector panel 214 controls the pressure drop across the membrane. These levels may include: off, low, medium, and high. Alternatively, the vacuum level may be continuously variable. Being able to select from a variety of different vacuum levels has shown to be useful, as samples which create a significant emulsion can be quite easily broken if no vacuum is used. Once the emulsion has broken, then the vacuum setting can be increased to significantly reduce the sample process time. For example, 10 ml of methylene chloride may take about 4 minutes to flow through with a 5" Hg vacuum, but the same sample through the same membrane may only take 15–20 second at 6" Hg. This is a significant time savings.

A controller 216 coupled to the vacuum 212 can be added that will vary the pressure drop across the membrane as a function of time. For example, the controller 216 can be programmed to have an initial predetermined period of time during which no vacuum or a very low first predetermined vacuum level is applied and a second predetermined period of time during which an increased second predetermined vacuum level is applied. The controller 216 can also be programmed to turn off the vacuum after a third predetermined period of time to prevent the apparatus from pulling residual water through the membrane. Given sufficient time, approximately 6–12 hours, any residual water on the surface of the membrane may "wet" the membrane and flow through with the organic solvent. Therefore, there is a limited time window for allowing water to reside on the membrane, but this time is not a problem for the application that this device will be used for.

In addition, testing has shown that draining the emulsion directly into the membrane reservoir aids with the breaking of emulsions. Once the emulsion has broken, if the analyst desires, after each drying step, the retained water and emulsion can be poured back into the separatory funnel for additional extractions. This could possibly significantly increase recovery values.

Figure 3:
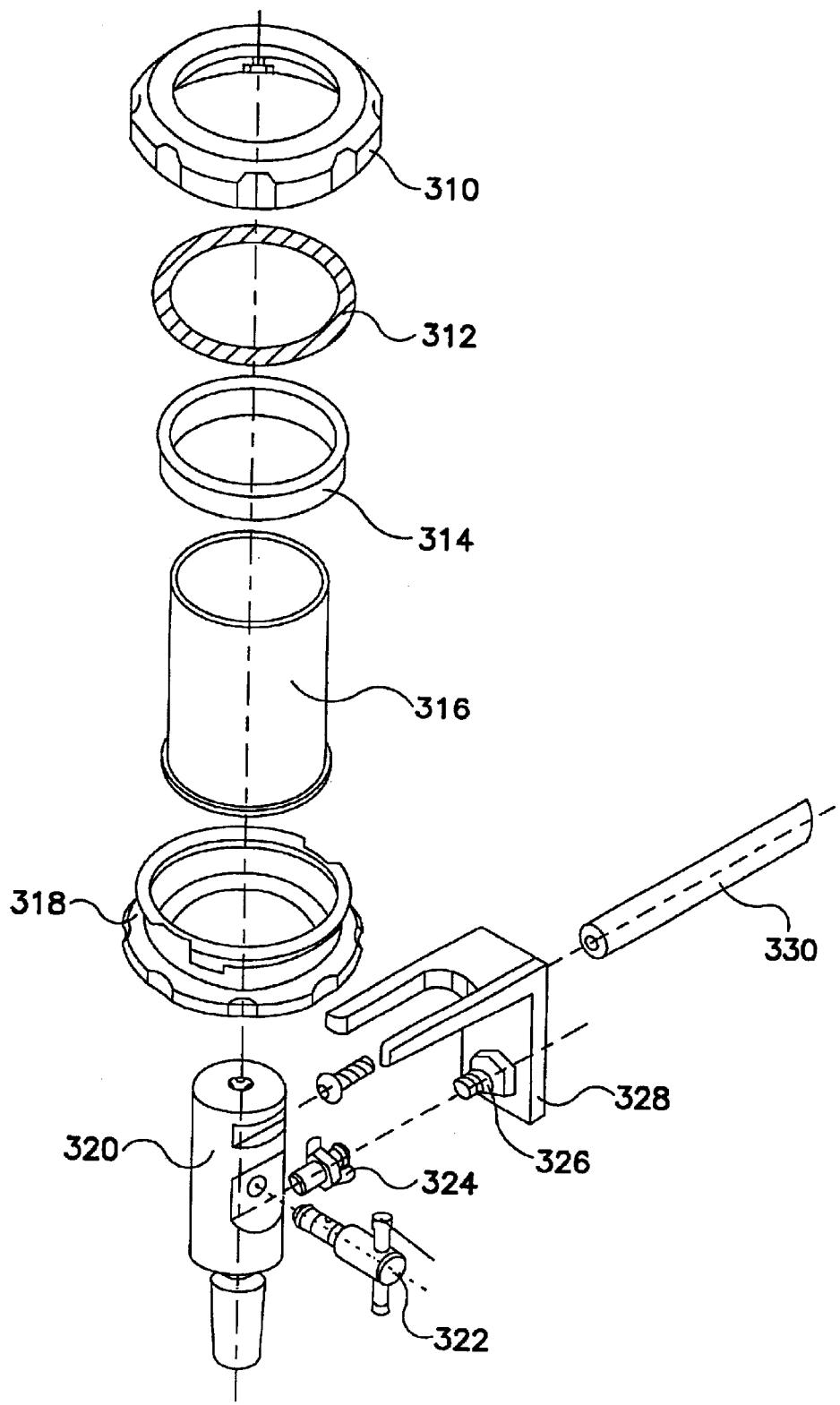
FIG. 3 is an exploded view of a preferred separator apparatus in accordance with the present invention.

As noted, FIG. 3 is an exploded view of a preferred separator apparatus in accordance with the present invention. More specifically, as shown therein there can be seen locking ring 310, wave spring 312, thrust ring 314, reservoir 316, base 318 for membrane and screen (not shown), stopcock 322, shut-off connectors 324 and 326 (through which vacuum may be applied), bracket 328 and support rod 330.

In yet another alternative embodiment, the invention herein relies upon the use of single layer of fluropolymer material. More specifically, with reference to FIG. 1, the fluropolymer layer 105 can be completely eliminated, and fluropolymer layer 104 is then used on its own to provide efficient water separation. In such embodiment, fluropolymer layer 104 is preferably selected from an expanded fluropolymer membrane. By expanded fluropolymer it is meant that, among other things, the fluropolymer can be characterized by one or more of the following properties:.

IPA Bubble Point: $\geq 25$ psi, preferably 28.8 psi

Alcohol Flow: 60–70 seconds (100 mls of isopropanol at 27.5" Hg through a 47 mm disk)

Water Entry Pressure: 100 psi (pressure at which water first breaks through the membrane)

To confirm the advantage of the above referenced single layer expanded type membrane, a side-by-side comparison was made with respect to membranes of the prior art. Specifically the expanded fluropolymer membrane was placed in the apparatus of FIG. 1, without fluropolymer layer 105. Water was positioned on top of the membrane in column 102 along with about 5 ml of methylene chloride solvent. A vacuum of 15" Hg was applied to the bottom side of the membrane. After about 3–5 minutes, additional solvent was added, and when no water past through the membrane the vacuum level was increased to 16" Hg. This was repeated until reaching a vacuum of about 22" Hg. At this vacuum level, water began to pass through the membrane. This was observed by use of colored water.

The above experiment was repeated with a membrane sold under the tradename "Zelfluor", as disclosed in U.S. Pat. No. 5,268,150, and it was observed that the water began to break through such membrane at about 8" Hg. Accordingly, such side-by-side comparison confirms that the membrane herein is able to provide sufficient water removal at much higher vacuum levels.

In addition, yet another side-by-side comparison was conducted with a similar commercially available fluropolymer membrane of the prior art. Specifically, a fluropolymer membrane available from Lab Glass as part # C3918-47, which is another example of a cast fluropolymer membrane material. In this test, the IPA Bubble Point was determined, which is a relative measure of pore size. The membrane is wetted with isopropyl alcohol and air pressure is applied until a stream of air bubbles are seen. The results are listed below:

| Test | Prior Art Membrane | Expanded Fluropolymer Membrane |
|---|---|---|
| IPA Bubble Point | 8–10 psi | $\geq 25$ psi |

As can be seen the expanded fluropolymer membrane herein demonstrates a higher pressure in the IPA Bubble Point test, thereby indicating that the tested prior art membrane has much larger pore size.

Finally, yet another side-by-side test was conducted to confirm that unique advantage in the selection of the expanded fluropolymer membrane material of the present invention over the conventional cast membranes noted above. In this test, water entry pressure was evaluated, which evaluated the water pressure necessary for water to break through the membrane material. The cast membranes of the prior art indicated a water pressure of about 6 psi. The expanded type PTFE membranes herein demonstrated a water pressure necessary for break through of $\geq 60$ psi.

It should be understood that, while the present invention has been described in detail herein, the invention can be embodied otherwise without departing from the principles thereof, and such other embodiments are meant to come within the scope of the present invention as defined in the following claims.

What is claimed is:

1. A method for separating residual water from a solvent, comprising the steps of:

providing a reservoir containing a solution comprising solvent containing residual water, the reservoir having an opening to allow the solution to drain from the reservoir, resisting the flow of the solution from the reservoir with a hydrophobic membrane layer comprising a layer of fluropolymer material, said membrane material having an IPA Bubble Point of $\geq 25$ psi, said membrane positioned in series with the reservoir opening, decreasing the pressure on the second side of said membrane relative to the first side of said membrane to thereby increase the flow rate of the solvent through the membrane; therein removing said water from said solvent to provide a solvent with a water level of less than or equal to 1.0 ppm.

2. The method of claim 1 wherein said fluropolymer comprises PTFE.

3. The method of claim 2 wherein said PTFE has a thickness of about 1–5 mils.

4. The method of claim 1 wherein the step of decreasing the pressure on the membrane is done by applying a vacuum.

5. The method of claim 4 wherein the vacuum is varied.

6. The method of claim 4 wherein the vacuum is greater than 8" Hg.

7. The method of claim 6 wherein the vacuum is greater than 8" Hg and up to 22" Hg.

8. The method of claim 1 wherein the decreasing of the pressure is delayed a selected period of time.

9. A method for separating residual water from a solvent, comprising the steps of:

providing a reservoir containing a solution comprising solvent containing residual water, the reservoir having an opening to allow the solution to drain from the reservoir, resisting the flow of the solution from the reservoir with a membrane layer comprising a first layer of hydrophobic fluropolymer material, said membrane positioned in series with the reservoir opening, said membrane material having an IPA Bubble Point of $\geq 25$ psi, where said membrane is supported on a screen layer, decreasing the pressure on the second side of said supported membrane relative to the first side of said supported membrane to thereby increase the flow rate of the solvent through the membrane;

therein removing said water from said solvent to provide a solvent with a water level of less than or equal to 1.0 ppm.

10. The method of claim 9 wherein said screen layer comprises a fluropolymer polymer.

11. An apparatus for separating residual water from a solvent, comprising:

a reservoir containing a solution comprising solvent containing residual water, the reservoir having an opening to allow the solution to drain from the reservoir, a hydrophobic membrane layer comprising a layer of fluropolymer material said membrane material having an IPA Bubble Point of ≧25 psi, said membrane positioned in series with said reservoir opening, a device for generating vacuum on said fluropolymer material, wherein said solvent containing water passes through said membrane layer therein removing water from said solvent to provide a solvent with a water level of less than or equal to 1.0 ppm.

12. A method for separating residual water from a solvent, comprising the steps of:

providing a reservoir containing a solution comprising solvent containing residual water, the reservoir having an opening to allow the solution to drain from the reservoir, resisting the flow of solution from the reservoir with a hydrophobic membrane layer comprising a layer of fluropolymer material having an IPA Bubble Point of ≧25 psi, said membrane also demonstrating a water pressure necessary for break-through of water through said membrane of ≧ 60 psi, said membrane positioned in series with the reservoir opening;

decreasing the pressure on the second side of said supported membrane relative to the first side of said supported membrane to thereby increase the flow rate of the solvent through the membrane;

therein removing said water from said solvent to provide a solvent with a water level of less than or equal to 1.0 ppm.

* * * * *

UNITED STATES PATENT AND TRADEMARK OFFICE
CERTIFICATE OF CORRECTION

PATENT NO. : 6,749,755 B2  Page 1 of 1
APPLICATION NO. : 10/095296
DATED : June 15, 2004
INVENTOR(S) : Johnson It is certified that error appears in the above-identified patent and that said Letters Patent is hereby corrected as shown below:

Title Page, Item (56) References Cited: Add U.S. Patent No. --5,552,023, 9/1996 Zhou, 203/18--.

Title Page, Item (56) References Cited: Add U.S. Patent No. --5,066,403 11/1991 Dutta et al., 210/638--.

Signed and Sealed this

Twenty-first Day of November, 2006

JON W. DUDAS
*Director of the United States Patent and Trademark Office*